United States Patent
Kawai et al.

(10) Patent No.: US 6,492,303 B1
(45) Date of Patent: Dec. 10, 2002

(54) COMPOSITIONS FOR PROTECTING A PLANT FROM A DISEASE AND USING METHOD THEREOF

(76) Inventors: Hiroshi Kawai, 409-5, Yabata Chigasaki-shi, Kanagawa 253-0085 (JP); Rieko Kase, 9-1, Koishikawa 3-chome, Bunkyo-ku, Tokyo 112-0002 (JP)

( * ) Notice: Subject to any disclaimer, the term of this patent is extended or adjusted under 35 U.S.C. 154(b) by 0 days.

(21) Appl. No.: 09/787,724
(22) PCT Filed: Sep. 22, 1999
(86) PCT No.: PCT/JP99/05179
§ 371 (c)(1), (2), (4) Date: Apr. 9, 2001
(87) PCT Pub. No.: WO00/16622
PCT Pub. Date: Mar. 30, 2000

(30) Foreign Application Priority Data

Sep. 22, 1998 (JP) ............................................ 10-268709

(51) Int. Cl.⁷ ............................................... A01N 37/00
(52) U.S. Cl. ....................................... 504/142; 504/307
(58) Field of Search ............................. 504/116.1, 142, 504/307

(56) References Cited

FOREIGN PATENT DOCUMENTS

| JP | 55-72101 A | 5/1980 |
|----|------------|--------|
| JP | 60-190800 A | 9/1985 |
| JP | 5-331016 A | 12/1993 |
| JP | 8-333214 A | 12/1996 |
| JP | 9-175919 A | 7/1997 |
| JP | 10-36210 A | 2/1998 |
| JP | 10-236909 A | 9/1998 |

OTHER PUBLICATIONS

Lynch et al, Role of substrates and anoxia in the accummulation of soil ethylene, 1980, 12(4),363–7.*

Role of Substrates and Anoxia in the Accumulation of Soil Ethylene; J.M. Lynch and S.H.T. Harper, Soil Biol. Biochem. vol. 12, pp. 363 to 367, Pergamon Press Ltd. 1980.

* cited by examiner

*Primary Examiner*—Alton Pryor
(74) *Attorney, Agent, or Firm*—Weingarten, Schurgin, Gagnebin & Lebovici LLP

(57) ABSTRACT

An object of the present invention is to provide a composition for protecting a plant from a disease that is safe, at low cost, environment friendly, and improves the natural resistance of plant itself by inducing production of a phytoalexin, an antibacterial substance inherent to plant, and a using method thereof. For the above purpose the present invention employs said composition for protecting a plant from a disease comprised of at least one sulfur-containing amino acid selected from the group comprising methionine, cysteine, and cystine, and D-glucose in a mixed form. In a preferred embodiment of the present invention, it is sprayed on the aboveground part of a plant either undiluted or after dilution with water by 100,000 times, directly mixed with soil, or irrigated on a plant after dilution with water by 1–1,000,000 times.

23 Claims, 1 Drawing Sheet

COMPOSITIONS FOR PROTECTING A PLANT FROM A DISEASE AND USING METHOD THEREOF

The Application is a 371 of PCT/JP99/05179 filed Sep. 22, 1999.

FILED OF THE INVENTION

This invention relates to a composition for protecting a plant from a disease and a using method thereof. More particularly, it relates to a composition for protecting a plant from a disease that induces production of a phytoalexin by application to a plant and suppresses pathogenic plant bacteria, and further a method of applying said composition to a plant in order to induce production of a phytoalexin and suppress various pathogenic plant bacteria resulting in protection of a disease of plant.

BACKGROUND OF THE INVENTION

The present inventors have already found out that treatment of methionine to a rice plant is capable of inducing production of a phytoalexin that donates resistance to various diseases (Japanese Patent Application H09-44206). Treatment of methionine to a rice plant induces accumulation of phytoalexins such as Sakuranetin and Momilactone, and resultantly donates resistance to rice blight (*Pyricularia oryzae*) that is a representative disease of rice plants. However, the effect of using methionine alone has proved to be insufficient and occasionally led to an inability to exhibit a desired effect.

DISCLOSURE OF THE INVENTION

The primary object of the present invention is to provide a composition for protecting a plant from a disease that induces production of a phytoalexin by application to a plant and suppresses plant bacteria more effectively than using methionine alone, and can be used throughout the year. The secondary object of the present invention is to provide a method of applying said protecting composition to a plant in order to induce production of a phytoalexin, suppress plant bacteria, and resultantly protect a plant from plant diseases.

The present inventors found that combined use of sulfur-containing amino acids and D-glucose, not single use of sulfur-containing amino acids such as methionine, exhibits a superior effect for suppressing not only plant diseases including rice blight (*Pyricularia oryzae*) at the above-ground position, but also soil diseases such as damping-off, which led to the exhibition of much more effective protecting ability for plant diseases, and accomplished the present invention.

The present invention provides a composition for protecting a plant from a disease that induces production of a phytoalexin by application to a plant for the purpose of suppressing pathogenic plant bacteria, that is, a composition characterized by containing at least one amino acid selected from the group of sulfur-containing amino acids comprising methionine, cycteine, and cystine, and D-glucose in a mixed form. Preferably said composition contains methionine as a sulfur-containing amino acid. Likewise, the mixed ratio by weight of a sulfur-containing amino acid to D-glucose in said protecting composition is preferably within the range of 1:(50–0.001).

Furthermore, the present invention provides a method of using said composition for protecting a plant from a disease, characterized by spraying said composition on the above-ground part of a plant either undiluted or after dilution with water by 1–100,000 times. More particularly, the present invention provides a method of using said composition for protecting a plant from a disease characterized either by mixing said composition directly with soil or by irrigating said composition after dilution with water by 1–1,000,000 times.

Furthermore, the present invention provides a method of using said composition for protecting a plant from a disease characterized by powder-coating plant seeds with said composition either directly or after supporting on a carrier. Furthermore, the present invention provides a method of using said composition for protecting a plant from a disease characterized by impregnating plant seeds with aqueous solution of said composition diluted by 10–1,000,000 times

BRIEF DESCRIPTION OF THE DRAWINGS

The illustrative embodiments of the invention will be described with particularity hereafter.

BEST MODE FOR CARRYING OUT THE INVENTION

Figure 1:
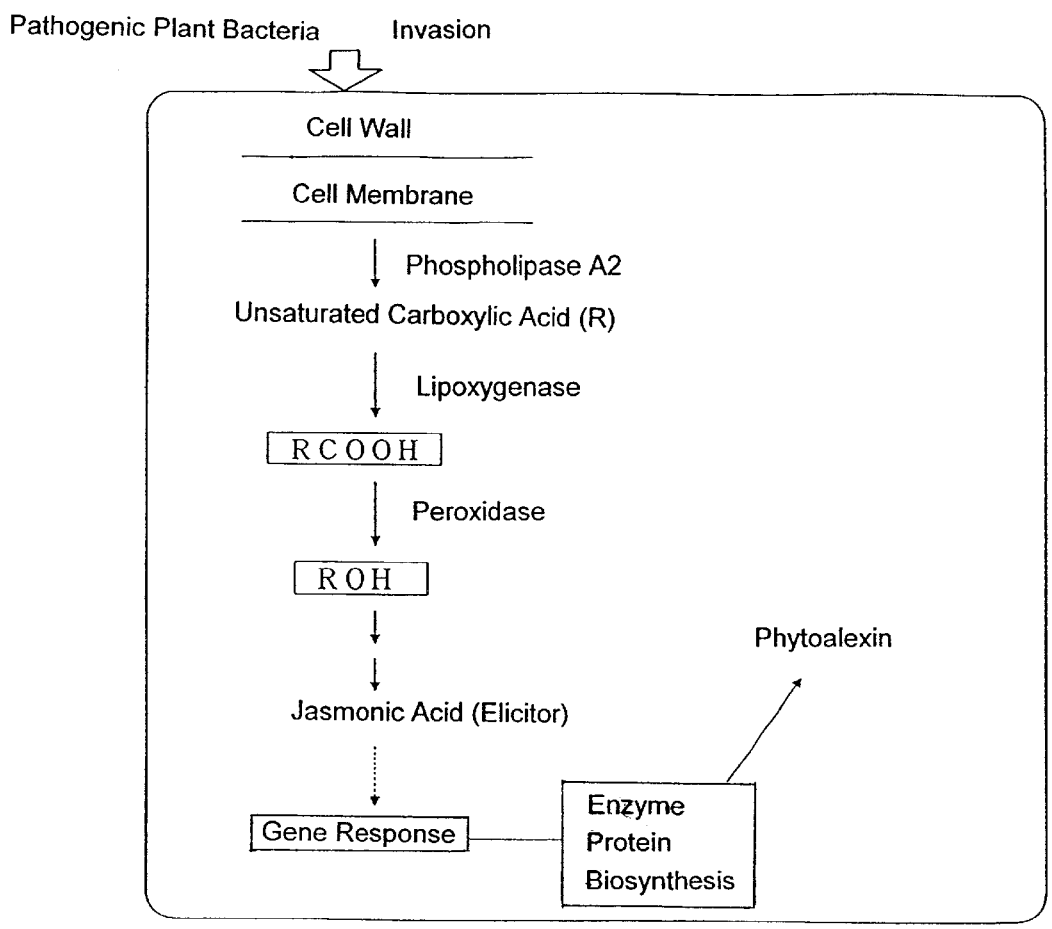
FIG. 1 illustrates the dynamic protection mechanism of plant against plant bacteria.

In the present invention the term "sulfur-containing amino acid" refers to at least one kind of sulfur-containing amino acids selected from the group comprised of methionine, cysteine, and cystine. These amino acids are not particularly limited in any manner. For example, any of L-methionine, DL-methionine, D-methionine, L-cysteine, DL-cysteine, D-cysteine, L-cystine, DL-cystine, L-cystine may be used. DL-methionine is most preferred in view of its lowest cost. The employed form is not limited in any manner: it may be a powder, an aqueous solution, or a dispersion of a sulfur-containing amino acid dispersed in a dispersion medium. In case amino acids are used as an aqueous solution, however, methionine or cysteine is preferred as the sulfur-containing amino acid since cystine is hardly soluble in water. The amount of sulfur-containing amino acids employed depends on the species of plant and the method of application, and may be determined accordingly.

D-glucose that is employed in the present invention is not particularly limited in any manner. Its employed amount may be determined appropriately depending on the species of plant and the method of application. The employed form is not limited in any manner: it may be a powder, an aqueous solution, or a dispersion of D-glucose dispersed in a dispersion medium. Depending on the production method, D-glucose may contain a part of other monosaccharides, oligosaccharides such as sucrose, maltose, and lactose, polysaccharides such as starch, cellulose, dextran, laminaran, and glycogen, as well as various glycosides. It can be used without difficulty unless the content of these compounds is within an area in which the effect of the present invention is not hurt.

The mixed ratio of sulfur-containing amino acids to D-glucose prepared for the purpose of the present invention is generally within the range of 1 to 50–0.001 by weight, preferably within the range of 1 to 10–0.01, most preferably 1 to 1–0.1. A ratio of sulfur-containing amino acids to D-glucose larger than 50 hampers the effect of sulfur-containing amino acids. A ratio of sulfur-containing amino acids to D-glucose less than 0.001 exhibits an insignificant effect similar to single use sulfur-containing amino acid, and thus is not preferred.

With regard to the amount of application for said composition according to the present invention, it is generally within the range of 10–30,000 g per 10 ares, preferably within the range of 50–5,000 g per 10 ares, more preferably within the range of 100–1,000 g. An amount of less than 1 g leads to an insignificant effect, and thus is not preferred. An amount of larger than 30,000 g exhibits unfavorable side effects such as yellowing of foliage and growth inhibition of roots, and thus is not preferred.

With regard to the method of application of said composition for protecting a plant from a disease at the above-ground part of a plant according to the present invention, the composition may be sprayed either undiluted or diluted with water by 1–100,000 times, preferably 1–10,000 times, most preferably 500–2,000 times. Dilution of more than 100,000 times leads to an insignificant effect. It is possible to employ said composition for protecting a plant from a disease according to the present invention in the form of direct mixing with soil or irrigating after dilution with water. In a latter case, it may be employed generally at dilution of 1–1,000,000 times with water, preferably at 1–100,000 times, most preferably at 500–10,000 times. Dilution of more than 1,000,000 times with water leads to an insignificant effect.

When the method of seed impregnation is adopted for said composition for protecting a plant from a disease according to the present invention, it may be employed at dilution of generally 10–1,000,000 times with water, preferably at 10–1,000,000 times, most preferably at 10–10,000 times. Dilution of less than 10 times might yield a chance of incomplete dissolution of the effective components, while at dilution of more than 1,000,000 times the necessary amount of the effective components might not be conveyed to the impregnated seeds within a prescribed time.

Concerning the application interval of said composition for protecting a plant from a disease according to the present invention, It is preferred to be applied every 3–14 days periodically in general. However, it is also possible to apply it every day or with a long interval depending on the stage of growth, the species of plant, or the situation of growth.

With regard to the amount of application, It is generally within the range of 10–10,000 ml per square meter. An amount of less than 10 ml exhibits an insignificant effect, and thus is not preferred. An amount of more than 10,000 ml frequently exhibits a side effect of excess damp to seedlings, and thus is not preferred. It may be applied preferably within the range of 100–5,000 ml per square meters, more preferably within the range of 300–2,000 ml. In a case of spraying in a main farm, it may be sprayed generally within the range of 1–500 L per 10 ares, preferably within the range of 10–300 L, more favorably within the range of 50–200 L. In a case of irrigating in a main farm, it may be irrigated generally within the range of 10–30,000 L per 10 ares, preferably within the range of 100–15,000 L, more favorably within the range of 1,000–10,000 L.

In a most preferred application method for the seedling period, it is applied at 500 ml per square meters in an irrigating form every five days starting from the period of 1.5 blades. After the seedlings are transplanted to a main farm, it may be irrigated preferably every ten days at 1,500 L. It is possible to combine agro-active ingredients such as antibacterial agents and insecticides, fertilizers, growth modifiers, viscosity modifiers, and surfactants, which are all noted for absence of sulfur-containing amino acids and D-glucose, with said composition for protecting a plant from a disease according to the present invention within a range in which the effect of the present invention is not hurt.

The agro-active ingredients employed in the present invention are not particularly limited. They may be used singly or in combination with two or more species at optional ratio. The following compounds are given as only examples. Note that the following names of agro-active ingredients are based on the general description in the Agrochemicals Handbook (published by Japanese Association of Plant Disease Prevention, 1989).

Examples of herbicides included in the present invention are; 2,4-D, MCP, MCPB, CNP, MCC, DCPA, CAN, Phenothiol, Cromeprop, Naproanilid, Crometoxinil, Benthiocarb, Biphenox, Esprocalp, Morinate, Dimepirate, Butachlor, Prethirachlor, Bromobutid, Mephenaset, Dymron, Bensulfronmethyl, Symmetrin, Brometrin, Dimethametrin, Bentazon, Oxadiazon, Pyrazorate, Pyrazoxifen, Benzofenap, Trifluralin, and Biperofos.

Examples of insecticides included in the present invention are; BRP, CVMP, PMP, PAP, DEP, EPN, NAC, MTMC, MIPC, BPMC, PHC, MPMC, XMC, MPP, MEP, Pyrimifosmethyl, Diazinon, Isoxathion, Pyridafenthion, Chlorpyrifosmethyl, Pamidthion, Marathon, Dimethoate, Ethylthiometon, Monochlotofos, Probafos, Bendaioaclp, Thiodicalp, Cycliprotolin, Ethofenprox, Kaltap, Thiocyclum, Bensultap, and Buprofezin.

Examples of antibacterial agents included in the present invention are; basic cupric sulfate, basic cupric chloride, cupric hydroxide, organic sulfuric salts of nickel, Thiraum, Captan, TPN, Furacide, IBP, EDDP, Thiofanatemethyl, Benomil, Iprodion, Mepronil, Furutranil, Teflofratam, Bencyclon, Metharaxil, Triflumizol, Brastcyzin-S, Kasugamycin, Polyoxin, VaridamycinA, Oxytetracycsin, Hydroxyisoxazol, methasulfocalp, MAF, MAEE, Benthiazol, Fenazinoxid, Dichlomezin, Propenazol, Isoprothioran, tricyclazol, pyrokiron, Oxonic Acid, and Guazatin.

Furthermore, it is possible to add plant growth modifiers such as Inavenfid, oxyethylenedokosanol, nicotinic acid amide, and benzylaminopurine.

The fertilizer component employed in the present invention is not particularly limited. Examples of fertilizers included in the present invention are; compost, barnyard manure, cattle excreta, human excreta, vegetation ash, tree ash, rice straw, wheat straw, rice husk, rice sugar, wheat sugar, pea pod, nitrogen fertilizers, phosphate fertilizers, potassium fertilizers, composite fertilizers, lime fertilizers, silicate fertilizers, magnesia fertilizers, manganese fertilizers, borate fertilizers, trace mineral compound fertilizers, organic fertilizers, fish refuse, droppings of poultry and cattle, processed dung of poultry and cattle, their burned ash, drain fertilizers, lime byproducts at sugar manufacturing, scraps of revolving furnace, shell lime powder, waste of agricultural products, refuse in food industry, waste of fermentation industry, dregs in fermentation, waste of textile industry, dregs in marine products industry, sludge of drainage, compost from urban trash, bone ash, etc. These fertilizer components may be employed singly or in combination with two or more species mixed at optional ratio. In addition to the above products, it is possible to combine soil modifiers such as zeolite, bentonite, vermiculite, peat, perlite, humic acid-based materials, charcoal, polyethyleneimine-based materials, and PVA-based materials.

Examples of surfactants in the present invention are; anionic surfactants including; alkylsulfosuccinic acid salts, condensated phosphate acid salts, alkylbenzenesulfonic acid salts such as dodecylbenzenesulfonic acid sodium salt, alkylnaphthalenesulfonic acid salts, formalin condensates of naphthalenesulfonic acid salts, ligninsulfonic acid salts, polycarboxylic acid salts, alkylethersulfuric acid salts, polyoxyethylene-alkylarylphenylether-sulfuric acid salts, polyoxyethylene-alkylarylether-sulfuric acid salts, polyoxyethylene-alkylaryl-sulfuric acid salts, polyoxyethylene-alkylarylether-sulfate ester salts, polyoxyethylene-alkylarylether-acetate ester-sulfuric acid salts. The salt form includes alkali-metal salts, ammonium salts, and amine salts.

Furthermore, examples of surfactants in the present invention include; nonionic surfactants such as; polyoxyethylene-alkylether, polyoxyethylene-alkylarylether, polyoxyethylene-alkylarylphenylether, polyoxyethylene-styrylphenylether, polyoxyethylene-alkyl ester, sorbitan-alkyl-ester, polyoxyethylene-sorbitanalkyl-ester, and polyoxyethylene-polyoxypropyleneglycol. It is possible to combine cationic surfactants with amphoteric ionic surfactants depending on the necessity. These surfactants may be employed singly or in combination with two or more species mixed at optional ratio.

It is thus possible to improve the resistance of a plant to a pathogenic disease by application (irrigating, etc. on a plant) of said composition for protecting a plant from a disease according to the present invention, which contains a mixture of sulfur-containing amino acids such as methionine and D-glucose, and by resultant acceleration in the production of a phytoalexin that is an antibacterial substance produced in the biosynthesis by plant itself.

EXAMPLES

While the invention will be described in detail and with reference to specific examples hereafter, it will be apparent to one skilled in the art that the present invention is not limited in any manner by examples thereof.

Example 1

DL-methionine (product of Wako Pure Chemicals Industry Company) was mixed with D-glucose (product of Wako Pure Chemicals) at a ratio of 1 to 50 by weight. The resultant mixture (a composition for protecting a plant from a disease according to the present invention) in 51 g was dissolved in distilled water for complete dissolution resulting in 1 litter of Solution MG1.

Example 2

DL-methionine (product of Wako Pure Chemicals) was mixed with D-glucose (product of Wako Pure Chemicals) at a ratio of 1 to 5 by weight. The resultant mixture (a composition for protecting a plant from a disease according to the present invention) in 6 g was dissolved in distilled water for complete dissolution resulting in 1 litter of Solution MG2.

Example 3

DL-methionine (product of Wako Pure Chemicals) was mixed with D-glucose (product of Wako Pure Chemicals) at a ratio of 1 to 1 by weight. The resultant mixture (a composition for protecting a plant from a disease according to the present invention) in 2 g was dissolved in distilled water for complete dissolution resulting in 1 litter of Solution MG3.

Example 4

DL-methionine (product of Wako Pure Chemicals) was mixed with D-glucose (product of Wako Pure Chemicals) at a ratio of 1 to 0.1 by weight. The resultant mixture (a composition for protecting a plant from a disease according to the present invention) in 1.1 g was dissolved in distilled water for complete dissolution resulting in 1 litter of Solution MG4.

Example 5

DL-methionine (product of Wako Pure Chemicals) was mixed with D-glucose (product of Wako Pure Chemicals) at a ratio of 1 to 0.01 by weight. The resultant mixture (a composition for protecting a plant from a disease according to the present invention) in 1.01 g was dissolved in distilled water for complete dissolution resulting in 1 litter of Solution MG5.

Example 6

DL-methionine (product of Wako Pure Chemicals) was mixed with D-glucose (product of Wako Pure Chemicals) at a ratio of 1 to 0.001 by weight. The resultant mixture (a composition for protecting a plant from a disease according to the present invention) in 1.001 g was dissolved in distilled water for complete dissolution resulting in 1 litter of Solution MG6.

Comparative Example 1

DL-methionine (product of Wako Pure Chemicals) in 1 g was dissolved in distilled water for complete dissolution resulting in 1 litter of Solution MG2.

Test 1

An examination was carried out for the study of influence of a mixture comprised of DL-methionine and D-glucose on the production of Sakuranetin and Momilactone-A, which are both phytoalexins for rice plants. The structural formula of Sakuranetin is shown in Formula 1, and of Momilactone-A in Formula 2.

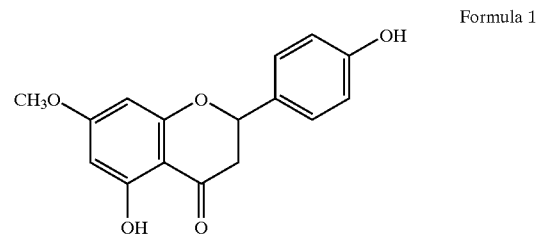

Formula 1

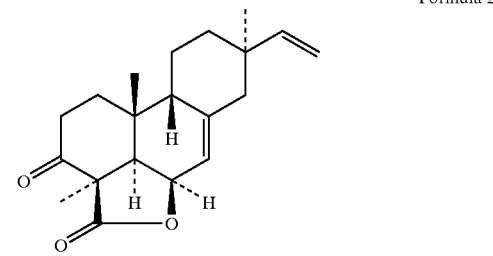

Formula 2

Test Material and Test Method

The tested species of rice plant was "Nihonbare". The seedlings were raised in a paper pot filled with soil containing 14 g of a compound fertilizer (N:P:K=10:6:8) until the age of 3.5 blades. Then they were transplanted into Wagner pots of 1/5,000a in three pieces each. The above compound fertilizer (N:P:K=10:6:8) was applied as the basic fertilizer into the whole layers in 7 g each. Then they were raised until the age of 7 blades in a greenhouse, and the fifth blades were selected as the testing material. The fifth blades were cut uniformly to a length of 20 cm, wounded for cuts in a diameter of 1 mm lined up on the central part of the foliage with an interval of 10 mm. They were put face down on a Kim-wipe moistened with distilled water in a plastic case. Then the Test Solutions were applied on the cuts of 1 mm by 25 μl respectively, capped with a transparent cover, and incubated for 60 hours at 25° C. under light. A control section was set up similarly except using 25 μl of distilled water only.

After 60 hours of incubation, the blades were cut out centering on the wounds with a cork borer to a size of 10 mm in diameter, and sent to an extraction process by 70% heated methanol together with the remaining test solution. The resultant liquids were condensed under reduced pressure, separated of the water layer, extracted again with diethyl ether, separated of the ether layer, and condensed to a dried state. The measurement of Sakuranetin was carried out by the normal phase TLC (with LKGDF SILICA GEL 60A, product of Wattman Company) using a mixed solvent (benzene:ethyl acetate:formic acid=10:1:1), eluted by ethyl acetate, condensed to a dried state, and then sent to a reversed phase HPLC (product of TOSO Company) measurement using a mixed solvent (methanol containing 0.2N formic acid:Solvent A=6:4, where Solvent A contains 2 g of $NaNO_3$ and 0.05 g of $H_2SO_4$ in 1,000 ml of water). Similarly the measurement of Momilactone-A was carried out through a BOND ELUT (C18, product of Varian Company), eluted by 80% methanol, and on a GC-MS/SIM (product of Nippon Denshi Company) instrument. The amount of generated Sakuranetin and Momilactone-A in each section is summarized in Table 1.

TABLE 1

|  | Amount of Sakuranetin | Amount of Momilactone-A |
| --- | --- | --- |
| Control Section | n.d. | n.d. |
| Section MG1 | 178.25 | 85.21 |
| SecUon MG2 | 211.25 | 95.07 |
| Section MG3 | 248.11 | 111.88 |
| Section MG4 | 241.90 | 112.08 |
| Section MG5 | 238.77 | 108.25 |
| Section MG6 | 203.31 | 86.13 |
| Comparative Section: |  |  |
| Section M1 | 122.56 | 55.89 |

Note: n.d. means not detected.

Unit: ng/spot (detected amount per cut)

Results of Test 1 and Discussions

In the control section in which only distilled water was treated, both Sakuranetin and Momilactone-A were not detected. In the Section M1, in which DL-methionine alone was treated as the comparison, Sakuranetin and Momilactone-A were detected at 122.56 ng/spot and 55.89 ng/spot (per one cut) respectively. On the other hand, the Sections MG1 to MG6, in which mixed solutions of methionine and D-glucose with different concentrations were treated, exhibited antibacterial activities almost twice as high as the comparative M1 (DL-methionine alone) for both Sakuranetin (activities in 178.25–248.11 ng/spot) and Momilactone-A (activities in 85.21–112.08 ng/spot) respectively.

FIG. 1 illustrates the dynamic protection mechanism of plant against pathogenic bacteria. Sakuranetin and Momilactone-A belong to the phytoalexin of rice plants. They are known generally as dynamic protecting substances against various pathogenic bacteria of plants including *Pyricularia oryzae*, and play an important role in the protection against invasion of pathogenic bacteria. The ED50 values of Sakuranetin and Momilactone-A are equally 15 ppm, which prove extraordinary antibacterial activities of the two compounds. The results in our present study suggest that a mixture of methionine and D-glucose (a composition for protecting a plant from a disease in the present invention) works better for controlling pathogenic diseases of plant than a solution of DL-methionine alone (M1).

Test 2

An examining test was carried out to investigate the influence of a mixture of methionine and D-glucose (a composition for protecting a plant from a disease according to the present invention) sprayed on the foliage upon the manifestation of rice blight (*Pyricularia oryzae*).

Test Material and Test Method

The tested species of rice plant was "Nihonbare". The seedlings were raised in a paper pot filled with soil containing 14 g of a compound fertilizer (N:P:K=10:6:8) until the age of 3.5 blades. Then they were transplanted into Wagner pots of 1/5,000a in three pieces each. The above compound fertilizer (N:P:K=10:6:8) was applied as the basic fertilizer into the whole layers in 7 g each. Then they were raised until the age of 8 blades in a greenhouse, and then presented to the testing. As a pretreatment, a prescribed solution of methionine and D-glucose (MG2) was sprayed on the foliage part in the Wagner Pots by 100 ml per foliage. A control section and a comparative section were set up similarly except using 100 ml of distilled water and 100 ml of M1 (solution of methionine alone) respectively.

After 24 hours following the pretreatment, the rice blight bacteria were inoculated on the whole aboveground part of all samples. Ten days after the inoculation, the infected area on the foliage was measured summing the necrosis section and the decay section per one square centimeter. The evaluation of total space of each foliage was determined using a space measurement apparatus of foliage. Then the infected sections were incorporated into an image analysis system through a microscope for the measurement of spaces.

The necrosis ratio (sum of necrosis area and decay area per total area) was determined for the Section MG2 (mixed solution of methionine and D-glucose), the Control Section, and the Comparative Section M1 (solution of methionine alone). They are shown in Table 2.

TABLE 2

|  | Control Section | Section M1 (methionine alone) | Section M2 (methionine/D-glucose mixed solution) |
| --- | --- | --- | --- |
| Necrosis Ratio | 25.1 | 7.8 | 1.8 |

Note: Necrosis Ratio = (necrosis area + decay area)/total area

Results of Test 2 and Discussions

Compared with the 25.1% necrosis ratio for the Control Section and 7.8% for the Section M1 (methionine alone), the Section MG2 (mixed solution of methionine and D-glucose) exhibited a high suppressing effect of MG2 against the manifestation of pathogenic spots in necrosis ratio of 1.8%. This is regarded the result of improved resistance against the invasion of pathogenic bacteria due to increased production of phytoalexins based on the treatment of MG2 (a mixed solution of methionine and D-glucose).

Test 3

An examining test was carried out to investigate the influence of a mixed solution of methionine and D-glucose (a composition for protecting a plant from a disease according to the present invention) upon the production of Solavetivone, an antibacterial substance found in the root part of eggplant belonging to the sesquiterpene. The structural formula of Solavetivone is shown in Formula 3.

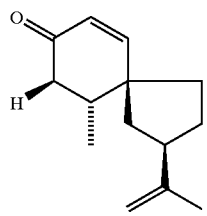

Formula 3

Test Material and Test Method

The tested species of eggplant was "Disease-resistant VF", which is usually used as a stock for eggplant. A cell-tray possessing 128 holes was filled with soil containing 7 g of a compound fertilizer (N:P:K=10:6:8). The seedlings of eggplant were raised in the tray until the age of 2 blades. Then they were transplanted into Wagner pots of 1/5,000a in one piece each. The above compound fertilizer (N:P:K=10:6:8) was applied as the basic fertilizer into the whole layers in 8 g each. Then they were raised until the age of 6 blades in a greenhouse, and then presented to the testing.

Each test section was set up in duplicate of 8. In the Test Section, a prescribed solution of methionine and D-glucose (MG3) was diluted ten-hold with water, and irrigated on the pots by 1 L per stock. Similarly city water was irrigated on the Control Section, a solution of methionine alone (0.01 WN %) on the Comparative Section (1), and a solution of D-glucose alone (0.01 WN %) on the Comparative Section (2).

One week after the treatment, the stocks were pulled out from the pots so as not to hurt the roots, washed carefully with distilled water, and cut out of the roots. The removed roots were extracted with a 70% ethanol solution (by 5-fold weight of roots) for 48 hours, and the filtrate was recovered using a filter paper. It was condensed at reduced pressure, extracted three times with an equal amount of ethyl acetate. The extracted solution was condensed, added of two-fold amount of hexane, passed through a column of Sep-Pak Light Silica that was pre-washed with hexane, eluted with hexane/ethyl acetate (2/1) to yield a resultant elute.

Solavetivone contained in the elute was analyzed using an HPLC (High Speed Liquid Chromatography) instrument equipped with a column of Intertsil ODS-2 under the following condition (flow rate: 1.0 ml/min, solvent: MeOH:water=65:45, detection: UV 245 nm). The results are shown by the content ($\mu$g) of Solavetivone in 1 g of eggplant roots.

The accumulated amounts of Solavetivone are summarized in Table 3.

TABLE 3

|  | Solavetivone (accumulated amount) |
| --- | --- |
| Control Section | 0.161 |
| Comparative Section (1), methionine alone | 0.220 |
| Comparative Section (2), glucose alone | 0.166 |
| Test Section, mixture of methionine and glucose | 0.483 |

Unit: $\mu$g/g (content of Solavetivone($\mu$g) in 1 g of eggplant roots)

Results of Test 3 and Discussions

Compared with the accumulation of Solavetivone in 0.161 $\mu$g/g for the Control Section (treated with city water), 0.220 $\mu$g/g for the Comparative Section (1) (methionine alone), and 0.166 $\mu$g/g for the Comparative Section (2) (D-glucose alone), the Test Section exhibited a prominent accumulation of Solavetivone in 0.483 $\mu$g/g (eggplant roots).

Solavetivone was recently discovered in eggplants as an antibacterial substance resistant generally against *Verticillium dahliae*, *Fusarium oxysprorum*, and *Pseudomonas solanacearum*. It is known to accumulate heavily in the roots of *Solanum aethiopicum* (a wild species close to eggplant) and *Solanum torvum*. The results in the present study suggest that a mixture of methionine and D-glucose (a composition for protecting a plant from a disease according to the present invention) strengthens the chemical mechanism of protection against plant diseases (and soil diseases) in comparison with the treatments using methionine solution or D-glucose solution only.

Test 4

An examination was carried out for the study of influence of a mixture comprised of methionine and D-glucose (a composition for protecting a plant from a disease according to the present invention) on the production of an antibacterial substance contained in the roots of corn.

Test Material and Test Method

Corn was seeded in a large-sized planter, raised until a height of 80 cm, and presented for the testing. Each test section was set up in duplicate of ten. In the Test Section, a prescribed solution of methionine and D-glucose (MG3) was diluted ten-hold with water, and irrigated on the planter by 3 L per stock. Similarly city water was irrigated on the Control Section.

One week after the treatment, the stocks were pulled out from the planter so as not to hurt the roots, washed carefully with distilled water, and cut out of the roots. The removed roots were extracted with a 70% ethanol solution (by 5-fold weight of roots) for 48 hours, and the filtrate was recovered using a filter paper. It was condensed and extracted with diethyl ether and ethyl acetate successively. Antibacterial activities of the extracted fractions were analyzed by the following method.

The extract (15 mg) was mixed with 15 ml of culture made of potato dextrose in a test tube so that the concentration of the extract became 1,000 ppm, and moved to a Petri dish. On the central part of the Petri dish, the testing bacteria (*Fusarium oxysporum*) were inoculated, and the dish was cultured for two weeks at 25° C. Then the diameter of the colony was measured. The growth degree (%) of the testing bacteria for the Test Section was determined assuming that the growth degree (diameter in cm) of the Control Section is 100. The test results are shown in Table 4.

TABLE 4

|  | Growth Degree of *F. oxysporum* (%) |
| --- | --- |
| Fraction of ether extract | 32 |
| Fraction of ethyl acetate extract | 71 |

Results of Test 4 and Discussions

It was confirmed in the above test results that the roots of corn treated with a prescribed solution of methionine and D-glucose (MG3) contain a substance that hinders the growth of the testing bacteria (*Fusarium oxysporum*). Both cultures containing the fraction of ether extract and the fraction of ethyl acetate extract were shown to hinder the growth of the bacteria, but the investigation of the fraction of ether extract, which showed stronger inhibition, indicated the existence of p-coumaric acid and 6-methoxy-benzoxazoline (MBOA). The structural formula of p-coumaric acid and MBOA is illustrated in Formula 4 and 5 respectively.

Formula 4

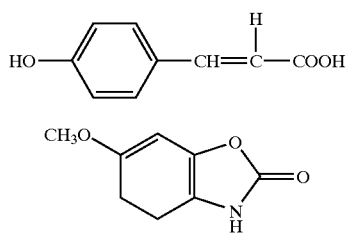

Formula 5

It is widely known that corn is effective in various soil diseases when used as a pre-breeding species in a cyclic breeding system. To be precise, the ground surveys in various test farms have shown that the intermediate breeding of corn exhibits a suppressing effect against plant diseases such as *Fusarium oxysporum*, Phythium sp., *Rhizoctonia solani*, and *Cephalosporium gregatum*. The test results in the present study suggest that a mixture of methionine and D-glucose (a composition for protecting a plant from a disease according to the present invention) increases the amount of antibacterial substances contained in the roots of corn, and suppresses bacteria that invoke soil diseases.

Test 5

An examination was carried out for the study of influence of a mixture comprised of methionine and D-glucose (a composition for protecting a plant from a disease according to the present invention) which is sprayed on the foliage of a plant, on the production of major phytoalexins found in plants such as podded peas, soybeans, beats, potatoes, carrots, Chinese cabbages, tomatoes, grapes, and tobaccos.

Test Material and Test Method

Above plants in the age of 5–6 blades were employed for the test. The Non-treating Section, the Test Section treated with a prescribed solution of methionine and D-glucose (MG3), and the Comparative Section (M1) treated with a solution of methionine alone were set up in duplicate of ten respectively. The application for MG3 and M1 was executed in the form of spraying on the foliage by 500 ml per stock. The analysis of phytoalexins were carried out by sampling the aboveground part of plants 72 hours after the spraying, extracting the samples with acetone followed by chromatographic elution with ethyl acetate through a silica gel, and finally analyzing on an HPLC instrument. The obtained results are shown in Table 5 assuming that the produced amount of phytoalexins per unit weight in the Non-treating Section is 100.

TABLE 5

| Phytoalexin (Plant name) | Section treated with Methionine/glucose mixture | Section treated with Methionine alone |
| --- | --- | --- |
| Pisatin (Podded pea) | 6,088 | 4,522 |
| Griceorin (Soybean) | 2,525 | 1,910 |
| Vetablugarin (Beat) | 2,387 | 1,810 |
| Ricitin (Potato) | 1,120 | 590 |
| 6-Methoxymelain (Carrot) | 6,015 | 3,222 |
| Blacinin (Chinese cabbage) | 27,818 | 18,600 |
| Ricitin (Tomato) | 28,975 | 10,039 |

TABLE 5-continued

| Phytoalexin (Plant name) | Section treated with Methionine/glucose mixture | Section treated with Methionine alone |
| --- | --- | --- |
| Lubimin (Eggplant) | 25,385 | 23,070 |
| α-Vinipherin (Grape) | 1,983 | 962 |
| Capsydiol (Tobacco) | 5,750 | 1,907 |

Results of Test and Discussions

Table 5 exhibits that the spraying of a prescribed solution of methionine and D-glucose (MG3) induces production of phytoalexins by 1.1–3 times compared with the spraying of methionine alone.

Test 6

An examination was carried out for the influence of a mixture comprised of methionine and D-glucose (a composition for protecting a plant from a disease according to the present invention) on a disease of potato. The tested species of potato was "Danshaku (Baron)". The seedlings were raised in a pot having a diameter of 30 cm until a height of 30 cm, and presented for the testing.

A prescribed solution of methionine and D-glucose (MG3) was diluted twofold, and sprayed on the foliage of the testing pods by 50 ml per pod. Three days after the spraying, the pathogenic bacteria (Race O) were inoculated in a suspension of planospore, and kept for 24 hours in a damp room. The index of manifestation for the disease was investigated 5 days later based on the following formula, $$\text{Index of Manifestation} = \frac{\sum ini}{4n} \times 100$$

where i, n, and ni denote the following.
  i: Index of Manifestation shown in Table 6
  n: Number of foliage tested
  ni: Number of foliage with the Index of Manifestation i.

TABLE 6

| Index of Manifestation i | Diameter of Pathogenic Part |
| --- | --- |
| 0 | not detected |
| 1 | less than 5 mm |
| 2 | 5–10 mm |
| 3 | 10–15 mm |
| 4 | More than 15 mm |

The manifestation ratio (%) is shown in Table 7

TABLE 7

| | Manifestation Ratio (%) |
| --- | --- |
| Non-treated Section | 30.0 |
| Section treated with the Prescribed solution | 11.0 |

Results of test 6 and discussions

The Table 7 indicates that the spraying of a prescribed solution of methionine and D-glucose (MG3) effects to suppress the growth of a pathogenic disease of potato.

Test 7

An examination was carried out for the effect on the mildew of tomato. The tested species of tomato was "Zuiken". A prescribed solution of methionine and D-glucose (MG3) was sprayed on the foliage of the testing seedlings in the age of 5–6 blades by 50 ml per stock. Three days after the spraying, the mildew (*Leveillula Taurlca*) were inoculated in the form of spraying, and investigated 10 days later for the manifestation as is shown in Table 8.

TABLE 8

|  | Manifestation ratio (%) |
| --- | --- |
| Non-treated section | 18.1 |
| Section treated with the prescribed solution | 0.3 |

Results of test 7 and discussions

As seen in Table 8, it was confirmed that the spraying of a prescribed solution of methionine and D-glucose (MG3) effects to suppress the growth of the mildew disease of tomato.

Test 8

An examination was carried out for the effect on alternaria leaf spot of apple. The tested trees of apple were young trees of "Tsugaru" at age two. The testing scale was set to 5 trees per section in duplicate of two. The spraying of a prescribed solution of methionine and D-glucose (MG3) diluted five-fold was carried out by 2 L per stock at six times (on June 15, June 25, July 10, August 6, August 15, and August 25). The measurement for the disease was carried out on September 1, calculating the number of pathogenic spots in the total extended leaves. The result is shown in Table 9.

TABLE 9

|  | Number of pathogenic spots per foliage |
| --- | --- |
| Non-treated Section | 34 |
| Section treated with the prescribed solution | 10 |

Results of Test 8 and Discussions

As seen in Table 9, it was confirmed that the spraying of a prescribed solution of methionine and D-glucose (MG3) effects to suppress the growth of alternaria leaf spot of apple.

Test 9

An examination was carried out for the effect of powder coating of seeds with a mixture of methionine and D-glucose (a composition for protecting a plant from a disease according to the present invention) on damping-off of cucumber.

Test Material and Test Method

Specific soil was taken from a farm showing frequent occurrence of damping-off of cucumber. It was filled in poly-pots with a diameter of 90 mm, and presented for the testing. To a mixture of 10 g methionine and 2 g D-glucose, a powder of silica was added in 10 g, and mixed thoroughly. The seeds of cucumber were moistened, and powder-coated with the above powder, and seeded in one seed per pot. In the Control Section the non-treated seeds were seeded in one seed per pot similarly. The each Test Section was comprised of 100 pots. Three weeks after the seeding, the pots were investigated for the occurrence of damping-off. The test results are shown in Table 10.

TABLE 10

|  | Occurrence (%) of "damping-off" |
| --- | --- |
| Non-treated Section | 34 |
| Section treated with the mixture of methionine and D-glucose | 10 |

Results of Test 9 and Discussions

As seen in Table 10, it was confirmed that the powder coating of cucumber seeds with a mixture of methionine and D-glucose (a composition for protecting a plant from a disease according to the p resent invention) effects to suppress the occurrence of damping-off of cucumber.

Test 10

An examination was carried out for the influence of impregnating seeds of cucumber with a nixed solution of methionine and D-glucose (a composition for protecting a plant from a disease according to the present invention) on damping-off of cucumber.

Test Material and Test Method

Specific soil was taken from a farm showing frequent occurrence of damping-off of cucumber. It was filled in poly-pots with a diameter of 90 mm, and presented for the testing. Cucumber seeds were impregnated in a prescribed solution of methionine and D-glucose (MG5) for 5 hours, and seeded in one seed per pot. In the Non-treated Section the seeds were impregnated in city water for 5 hours, and seeded in one seed per pot similarly. The each Test Section was comprised of 100 pots. Three weeks after the seeding, the pots were investigated for the occurrence of damping-off. The test results are shown in Table 11.

TABLE 11

|  | Occurrence (%) of "damping-off" |
| --- | --- |
| Non-treated Section | 32 |
| Section treated with the Prescribed solution | 12 |

Results of Test 10 and Discussions

As seen in Table 11, it was confirmed that the impregnation of cucumber seeds with a prescribed solution of methionine and D-glucose (MG5) effects to suppress the occurrence of damping-off of cucumber.

Example 7

A mixture of L-cysteine (product of Nippon Rikagaku Yakuhin) and D-glucose (product of Wako Pure Chemicals) was prepared in 1:1 (wt). The mixture (a composition for protecting a plant from a disease according to the present invention) in 2 g was dissolved completely in distilled water to make up 1 L of the test solution (CG1).

Example 8

A mixture of L-cysteine (product of Nippon Rikagaku Yakuhin) and D-glucose (product of Wako Pure Chemicals) was prepared in 1:0.1 (wt). The mixture (a composition for protecting a plant from a disease according to the present invention) in 11 g was dissolved completely in distilled water to make up 1 L of the test solution (CG2).

Comparative Example 2

L-cysteine (product of Nippon Rikagaku Yakuhin) in 1 g was dissolved completely in distilled water to make up 1 L of the test solution (C1).

Comparative Example 3

D-glucose (product of Wako Pure Chemicals) in 1 g was dissolved completely in distilled water to make up 1 L of the test solution (GL1).

Comparative Example 4

A mixture of L-proline (product of Wako Pure Chemicals) and D-glucose (product of Wako Pure Chemicals) was prepared in 1:1 (wt). The mixture (a composition for protecting a plant from a disease according to the present invention) in 2 g was dissolved completely in distilled water to make up 1 L of the test solution (PG1).

Comparative Example 5

A mixture of L-tryptophan (product of Wako Pure Chemicals) and D-glucose (product of Wako Pure Chemicals) was prepared in 1:1 (wt). The mixture (a composition for protecting a plant from a disease according to the present invention) in 2 g was dissolved completely in distilled water to make up 1 L of the test solution (TG1).

Comparative Example 6

A mixture of L-serine (product of Wako Pure Chemicals) and D-glucose (product of Wako Pure Chemicals) was prepared in 1:1 (wt). The mixture (a composition for protecting a plant from a disease according to the present invention) in 2 g was dissolved completely in distilled water to make up 1 L of the test solution (SG1).

Comparative Example 7

Glutathione of reduced type (product of Wako Pure Chemicals) in 2 g was dissolved completely in distilled water to make up 1 L of the test solution (GT1).

Comparative Example 8

Ammonium sulfate (product of Katayama Chemical) in 1 g was dissolved completely in distilled water to make up 1 L of the test solution (AS1).

Test 11

An examination was carried out for the study of influence of a mixture comprised of L-cysteine and D-glucose (a composition for protecting a plant from a disease according to the present invention) on the production of Sakuranetin and Momilactone-A, which are both phytoalexins for rice plants.

Test Material and Test Method

The tested species of rice plant was "Nihonbare". The seedlings were raised in a paper pot filled with soil containing 14 g of a compound fertilizer (N:P:K=10:6:8) until the age of 3.5 blades. Then they were transplanted into Wagner pots of 1/5,000a in three pieces each. The above compound fertilizer (N:P:K=10:6:8) was applied as the basic fertilizer into the whole layers in 7 g each. Then they were raised until the age of 7 blades in a greenhouse, and the fifth blades were selected as the testing material. The fifth blades were cut uniformly to a length of 20 cm, wounded for cuts in a diameter of 1 mm lined up on the central part of the foliage with an interval of 10 mm. They were put face down on a Kim-wipe moistened with distilled water in a plastic case. Then the Test Solutions were applied on the cuts of 1 mm by 25 µl respectively, capped with a transparent cover, and incubated for 60 hours at 25° C. under light.

After 60 hours of incubation, the blades were cut out centering on the wounds with a cork borer to a size of 10 mm in diameter, and sent to an extraction process by 70% heated methanol together with the remaining test solution. The resultant liquids were condensed under reduced pressure, separated of the water layer, extracted again with diethyl ether, separated of the ether layer, and condensed to a dried state. The measurement of Sakuranetin was carried out by the normal phase TLC (with LKGDF SILICA GEL 60A, product of Wattman Company) instrument using a mixed solvent (benzene:ethyl acetate:formic acid=10:1:1), eluted by ethyl acetate, condensed to a dried state, and then sent to a reversed phase HPLC (product of TOSO Company) measurement using a mixed solvent (methanol containing 0.2N formic acid:Solvent A=6:4, where Solvent A contains 2 g of $NaNO_3$ and 0.05 g of $H_2SO_4$ in 1,000 ml of water). Similarly the measurement of Momilactone-A was carried out through a BOND ELUT (C18, product of Varian Company), eluted by 80% methanol, and on a GC-MS/SIM (product of Nippon Denshi Company) instrument. The amount of produced Sakuranetin and Momilactone-A in each section is summarized in Table 12.

TABLE 12

|  | Amount of Sakuranetin | Amount of Momilactone-A |
| --- | --- | --- |
| Section CG1 | 182.36 | 79.86 |
| Section CG2 | 241.78 | 109.20 |
| Section C1 | 79.10 | 38.99 |
| Section GL1 | n.d. | n.d. |
| Section PG1 | n.d. | n.d. |
| Section TG1 | n.d. | n.d. |
| Section SG1 | n.d. | n.d. |
| Section GT1 | n.d. | n.d. |
| Section AS1 | n.d. | n.d. |

Results of Test 12 and Discussions

In the control section (Section C1) in which only L-cysteine was treated, both Sakuranetin and Momilactone-A were detected at 79.10 ng/spot and 38.99 ng/spot respectively. On the other hand, the Sections CG1 to CG2, in which mixed solutions of methionine and D-glucose with different concentrations were treated, exhibited excellent antibacterial activities for both Sakuranetin (activities in 182.36–241.78 ng/spot) and Momilactone-A (activities in 79.86–109.208 ng/spot) respectively. These values are better than the treatments of L-cysteine alone. Furthermore, both Sakuranetin and Momilactone-A were not detected for the Section GL1, in which only D-glucose was treated. In addition, experiments were carried out as the comparison for the mixtures of non-sulfur-containing amino acids and D-glucose. As the result, both Sakuranetin and Momilactone-A were not detected for the Test Sections of L-proline/D-glucose, L-tryptophan/D-glucose, and L-serine/D-glucose.

Furthermore, experiments were carried out as the comparison for the sulfur-containing substances such as glutathione and ammonium sulfate. As the result, both Sakuranetin and Momilactone-A were not detected with these compounds.

FIG. 1 has already shown the dynamic protection mechanism of plant against pathogenic bacteria. Sakuranetin and Momilactone-A, which belong generally to the phytoalexin of rice plants, are also known as dynamic protecting substances against various pathogenic bacteria of plants including *Pyricularia oryzae*, and play an important role in the protection against invasion of pathogenic bacteria. The ED50 values of Sakuranetin and Momilactone-A are equally 15 ppm, which prove extraordinary antibacterial activities of the two compounds. The results in our present study suggest that a mixture of L-cysteine and D-glucose (a composition for protecting a plant from a disease according to the present invention) works better for controlling pathogenic diseases of plant than a solution of L-cysteine alone (C1).

Industrial Applicability

The present invention relates to a method of preventing plant diseases that is characterized by high safety, low cost, environment-friendliness, and improving the natural resistance of plant against pathogenic diseases by inducing production of phytoalexins, which are defined as the antibacterial substances produced by plant itself. It is possible to suppress the plant diseases that deteriorate the harvest of a plant by application of said composition for protecting a plant from a disease according to the present invention and a using method thereof, and bring in resultantly an increase in the harvest.

What is claimed is:

1. A composition for protecting a plant from a disease that is applied on a plant for the purpose of suppressing pathogenic plant bacteria and induces production of a phytoalexin, consists essentially of at least one amino acid selected from the group of sulfur-containing amino acids and a saccharide in a mixed form.

2. A composition for protecting a plant from a disease according to claim 1, wherein said sulfur-containing amino acid is cysteine or cystine and said saccharide is D-glucose.

3. A composition for protecting a plant from a disease according to claim 2, wherein the mixed ratio of said sulfur containing amino acid to said D-glucose is within the range of 1:50 to 1:0.001 by weight.

4. A composition for protecting a plant from a disease according to claim 1, wherein said composition is sprayed on the aboveground part of a plant either undiluted or after dilution with water by 1–100,000 times.

5. A composition for protecting a plant from a disease according to claim 1, wherein said composition is either directly mixed with soil or irrigated on a plant after dilution with water by 1–1,000,000 times.

6. A composition for protecting a plant from a disease according to claim 1, wherein said composition is powder-coated on seeds of a plant either directly or after retention on a carrier.

7. A composition for protecting a plant from a disease according to claim 1, wherein said composition is dissolved in water of 1–1,000,000 times by weight, and seeds of a plant are impregnated in the resultant solution.

8. A composition for protecting a plant from a disease according to claim 2, wherein said composition is sprayed on the aboveground part of a plant either undiluted or after dilution with water by 1–100,000 times.

9. A composition for protecting a plant from a disease according to claim 2, wherein said composition is either directly mixed with soil or irrigated on a plant after dilution with water by 1–1,000,000 times.

10. A composition for protecting a plant from a disease According to claim 2, wherein said composition is powder-coated on seeds of a plant either directly or after retention on a carrier.

11. A composition for protecting a plant from a disease according to claim 2, wherein said composition is dissolved in water of 1–1,000,000 times by weight, and seeds of a plant are impregnated in the resultant solution.

12. A composition for protecting a plant from a disease according to claim 3, wherein said composition is sprayed on the aboveground part of a plant either undiluted or after dilution with water by 1–100,000 times.

13. A composition for protecting a plant from a disease according to claim 3, wherein said composition is either directly mixed with soil or irrigated on a plant after dilution with water by 1–1,000,000 times.

14. A composition for protecting a plant from a disease according to claim 3, wherein said composition is powder-coated on seeds of a plant either directly or after retention on a carrier.

15. A composition for protecting a plant from a disease according to claim 3, wherein said composition is dissolved in water of 1–1,000,000 times by weight, and seeds of a plant are impregnated in the resultant solution.

16. A process for protecting a plant from a disease comprising (a) preparing a mixture consisting essentially of a sulfur-containing amino acid and D-glucose and (b) applying said mixture to said plant or to the soil around said plant or to seeds used to grow said plant.

17. The process of claim 16 wherein said mixture is applied to a carrier before said mixture is applied.

18. The process of claim 16 wherein said mixture is diluted before use.

19. The process of claim 16 wherein said sulfur-containing amino acid is selected from the group consisting of methionine, cysteine, and cystine.

20. The process of claim 16 wherein the ratio of said sulfur-containing amino acid to D-glucose is within 1:50 to 1:0.001 by weight.

21. The process of claim 18 wherein said mixture is diluted with water by from 1:1 to 1:1,000,000 times.

22. The process of suppressing pathogenic plant bacteria comprising:

(a) preparing a mixture consisting essentially of a sulfur-containing amino acid and D-glucose and (b) applying said mixture to said plant or to the soil around said plant or to seeds used to grow said plant.

23. The process of inducing production of a phytoalexin comprising:

(a) preparing a mixture consisting essentially of a sulfur-containing amino acid and D-glucose and (b) applying said mixture to said plant or to the soil around said plant or to seeds used to grow said plant to produce phytoalexin.

* * * * *

UNITED STATES PATENT AND TRADEMARK OFFICE
CERTIFICATE OF CORRECTION

PATENT NO.      : 6,492,303 B1
DATED           : December 10, 2002
INVENTOR(S)     : Hiroshi Kawai et al.

It is certified that error appears in the above-identified patent and that said Letters Patent is hereby corrected as shown below:

<u>Title page, Item [54] and Column 1, line 1,</u>
Title, "COMPOSITIONS" should read -- COMPOSITION --;

<u>Column 3,</u>
Line 3, "less than 1" should read -- less than 10 --;

<u>Column 7,</u>
Line 37, "SecUon MG2" should read -- Section MG2 --;

<u>Column 9,</u>
Lines 30 and 31, "WN %)" should read -- W/V%) --; and

<u>Column 14,</u>
Line 5, "p resent" should read -- present --.

Signed and Sealed this

Sixteenth Day of December, 2003

JAMES E. ROGAN
*Director of the United States Patent and Trademark Office*